(12) United States Patent
Shaikh et al.

(10) Patent No.: US 8,449,838 B2
(45) Date of Patent: May 28, 2013

(54) DEVICES AND METHODS FOR BATCH PROCESSING MAGNETIC BEAD ASSAYS

(75) Inventors: Kashan Ali Shaikh, Clifton Park, NY (US); Christopher Michael Puleo, Glenville, NY (US); Jun Xie, Niskayuna, NY (US); Hansong Zeng, Schenectady, NY (US); Li Zhu, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 326 days.

(21) Appl. No.: 12/839,872

(22) Filed: Jul. 20, 2010

(65) Prior Publication Data

US 2012/0021931 A1 Jan. 26, 2012

(51) Int. Cl.
*B01L 3/00* (2006.01)
*G01N 33/533* (2006.01)

(52) U.S. Cl.
CPC .............. *B01L 3/00* (2013.01); *G01N 33/533* (2013.01)
USPC ........................................................ 422/502

(58) Field of Classification Search
None
See application file for complete search history.

(56) References Cited

PUBLICATIONS

Gassner et al., "Magnetic Forces Produced by Rectangular Permanent Magnets in Static Microsystems", Lab Chip, vol. 9, pp. 2356-2363, 2009.
Nagrath et al., "Isolation of Rare Circulating Tumour Cells in Cancer Patients by Microchip Technology", Letters, Nature, vol. 450, pp. 20-27, Dec. 2007.
Abonnenc et al., "Magnetic Track Array for Efficient Bead Capture in Microchannels", Anal Bioanal Chem, vol. 395, pp. 747-757, 2009.

*Primary Examiner* — Jim Ketter
(74) *Attorney, Agent, or Firm* — Fletcher Yoder, P.C.

(57) ABSTRACT

A microfluidic device for batch processing magnetic bead assays and having one or more microfluidic sample channels, comprising, one or more micromagnets seated in a fixture; and an actuator; wherein a portion of each micromagnet is in releasable operative association with one or more of the microfluidic sample channels, and another portion of each micromagnet is in releasable operative association with the actuator; and methods for using the same.

18 Claims, 10 Drawing Sheets

DEVICES AND METHODS FOR BATCH PROCESSING MAGNETIC BEAD ASSAYS

STATEMENT REGARDING FEDERALLY SPONSORED RESEARCH & DEVELOPMENT

This invention was made with Government support under contract number N00173-08-2-C003 that was awarded by the Navel Research Laboratory. The Government has certain rights in the invention.

BACKGROUND

The invention relates generally to microflow cytometry and more particularly to devices and methods for batch processing magnetic bead assays.

Flow cytometry is used in broad areas of technologies such as medical diagnostics. Such flow cytometers have generally been located in centralized laboratory settings and run by trained technicians. More recently laboratories are moving towards smaller, less expensive instruments that provide a greater level of automation. Microfluidics has played an important role in this transition, providing simpler methods of sample injection, cell sorting, and optical interrogation. However, sample preparation for these microdevices remains an unmet challenge before such devices are adapted for point-of-care and on-site environments.

For example, current magnetic bead based assays use a large permanent magnet that traps beads contained within microliter-sized tubes and wells for solution-based assays. These magnetic bead traps, that are meant to capture beads in a fluid flow, use the large permanent magnet for pre-concentration upstream from a standard flow cytometer. However, as with most bulk bead traps, detection limits are set by the reaction kinetics on the bulk surface used to capture beads. Current magnetic bead assays are inefficient at high bead counts because the beads clump together, which blocks binding sites on the beads. When performing surface reactions on beads trapped within continuous flow channels, bead clumping during magnetic bead immobilization interferes with surface binding reactions and downstream analysis. Although others have attempted to trap a small number of beads in parallel microfluidic reaction chambers for better control over bead reactions, this approach requires that the reactions take place in nanoliter-sized compartments, which severely limits throughput.

Others have also created magnetic arrays either using miniaturized electromagnets or passive arrays of permanent magnetic elements. However, electromagnets are too expensive and require too much power to employ them in magnetic bead assays. Similarly, passive arrays of permanent magnet elements are not practical for magnetic bead assays because the number of beads, on each magnet surface in a passive array on each individual magnetic surface, cannot be controlled. Thus, neither approach can be used to optimize and batch process magnetic bead reactions.

In addition, although studies have been conducted on flow cell arrays for capturing rare cells on arrays of immuno-functionalized posts, no methods exist to extend these studies to magnet bead-based approaches.

BRIEF DESCRIPTION

The arrays and methods of the invention substantially improve the efficiency of magnetic bead assays and provide a platform on which bead reactions may be optimized and batch processed by controlling the bead-to-target ratio and the loading and release of beads in discrete quantities. In one or more examples of the methods of the invention, a batch-mode process is used in which the bead to target ratio is controlled to ensure an efficient reaction. In addition, one or more examples of the methods of the invention may be adapted to process the magnets individually to allow batch processing of the beads post-reaction.

An embodiment of a microfluidic device of the invention for batch processing magnetic bead assays and having one or more microfluidic sample channels, generally comprises: one or more micromagnets seated in a fixture; and an actuator; wherein a portion of each micromagnet is in releasable operative association with one or more of the microfluidic sample channels, and another portion of each micromagnet is in releasable operative association with the actuator.

The actuator may comprise a primary magnet. The device may further comprise a mask that is configured to be variably interposed between one or more of the micromagnets and the primary magnet to control a magnetic attraction between one or more of the micromagnets and the primary magnet. The interposition of the mask may be varied based at least in part on a processing stage of a microfluidic assay. The microfluidic device may comprise a plurality of masks depending the configuration and may comprise a plurality of micromagnets and/or primary magnets.

The actuator of the microfluidic device may comprise a linear actuator. The linear actuator may comprise a primary magnet to which one or more of the micromagnets are in operative association. The micromagnets may be fixed to the primary magnet, and/or the device may comprise a mask that is configured to be variably interposed between one or more of the micromagnets and the primary magnet to control a magnetic attraction between one or more of the micromagnets and the primary magnet.

The micromagnets may be integrated into a microfluidic sample preparation module, wherein the module may be adapted to functionalize one or more magnetic beads. The microfluidic sample preparation module may be integrated into a flow cytometry system.

An example of a method of the invention for batch processing a microfluidic magnetic bead assay generally comprises: loading a plurality of magnetic microbeads into one or more microfluidic channels of a microfluidic device comprising a plurality of micromagnets; initiating the microbeads to flow across one or more of the micromagnets in the loaded channel; capturing one or more of the microbeads on one or more of the micromagnets; and releasing the captured beads, from one or more of the micromagnets, into the channel. The method may further comprise, initiating a flow of sample material into one or more of the channels and across one or more of the beads captured on the micromagnets, whereby at least a portion of the sample materials binds to one or more of the captured beads. The method may also further comprise, interposing a mask between a primary magnet and one or more of the micromagnets, to control a magnetic attraction between one or more of the micromagnets and the primary magnet.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The devices and methods of the invention in part optimize magnetic bead assays by generally subdividing a given assay into multiple sub-assays. Each sub-assay uses the optimal number of beads for a given assay and a given bead immobilization area. This batch process creates optimal conditions for each sub-assay and, depending on a given application, does not add appreciable time to the overall assay.

Magnetic bead assays within continuous sample flows involve immobilizing magnetic beads via a magnetic field, and then causing various reagents to flow across the beads to functionalize them with biological or chemical agents. There are optimal numbers of immobilized beads, above which a given assay typically loses efficiency. Above the optimal bead count, the beads are immobilized in a large clump and no longer confined just to one area. This bead clump prevents reagents from efficiently reaching beads on the inside of the clump during normal assay conditions. One or more of the examples of the methods of the invention address this problem effectively by dividing what would be a single, large bead assay into smaller, multiple sub-assays (otherwise referred to as a batch process), wherein each sub-assay uses the optimal number of beads. Each sub-assay uses a fraction of the total assay solutions while performing the normal assay operations. The beads are released for downstream analysis at the end of each sub-assay, preventing the buildup of beads in the immobilization area. The total number of sub-assays is substantially the same as what would typically be one full assay using current manual methods. This batch method becomes especially important in microfluidic reaction chambers, in which alternate reaction methods are insufficient.

Figure 1:
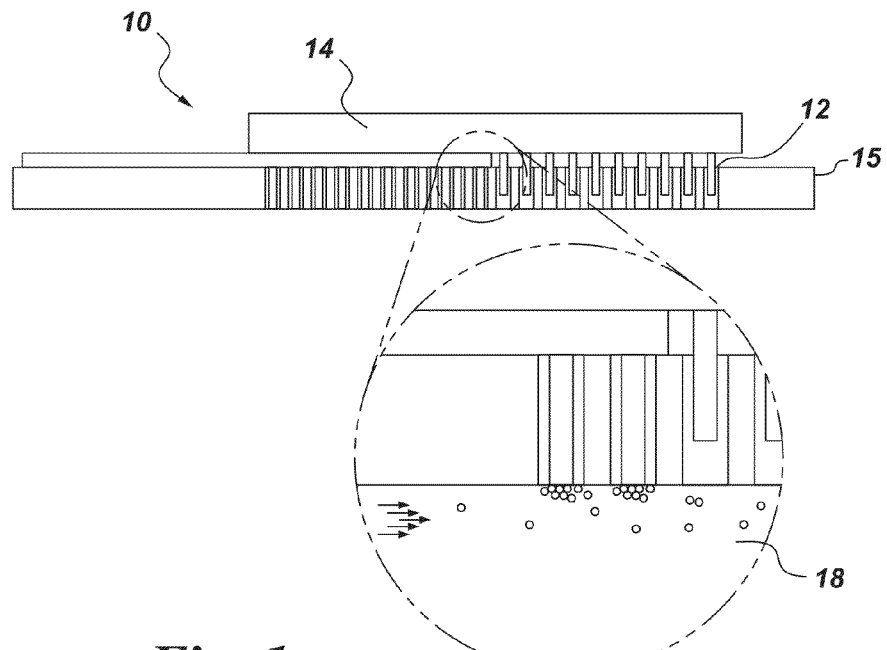
FIG. 1 is a schematic, side view, cross-sectional drawing of an embodiment of the magnet array of the invention during bead loading.
Figure 2:
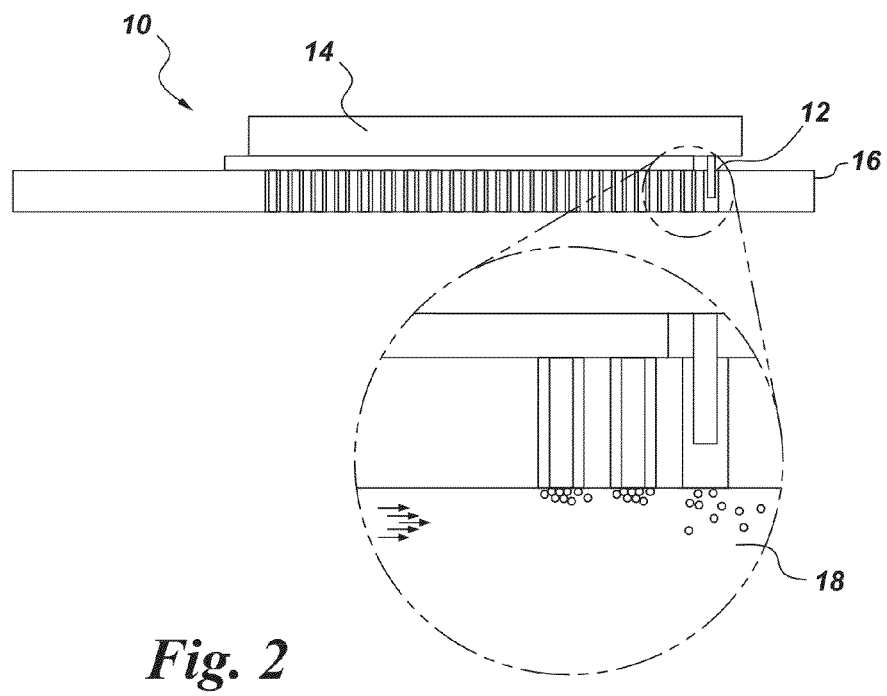
FIG. 2 is a schematic, cross-sectional drawing of the embodiment of FIG. 1 during bead release.
Figure 4:
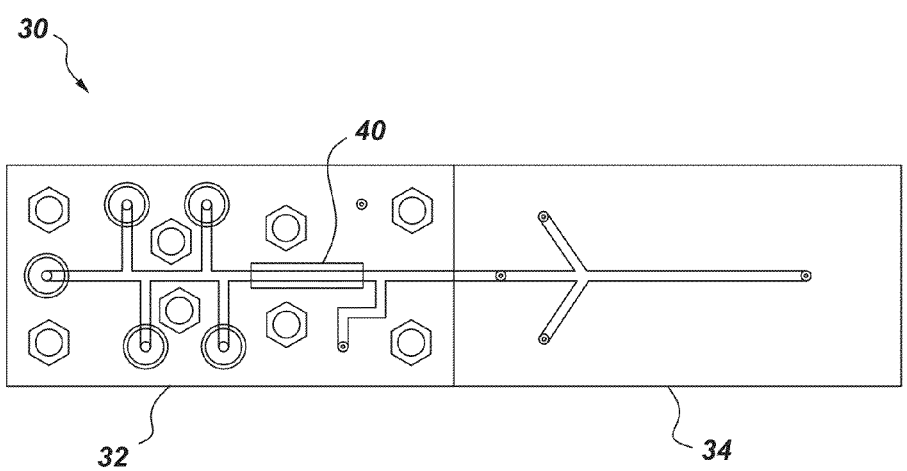
FIG. 4 is a schematic, cross-sectional drawing of another embodiment of the magnet array of the invention during bead release.
Figure 11A:
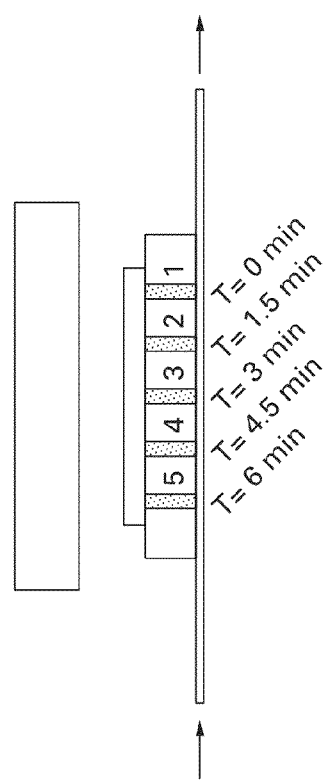
FIG. 11A is a schematic drawing an example of an array comprising five micromagnets and the loading times for each magnet, a predetermined times, to capture passing beads.
Figure 11B:
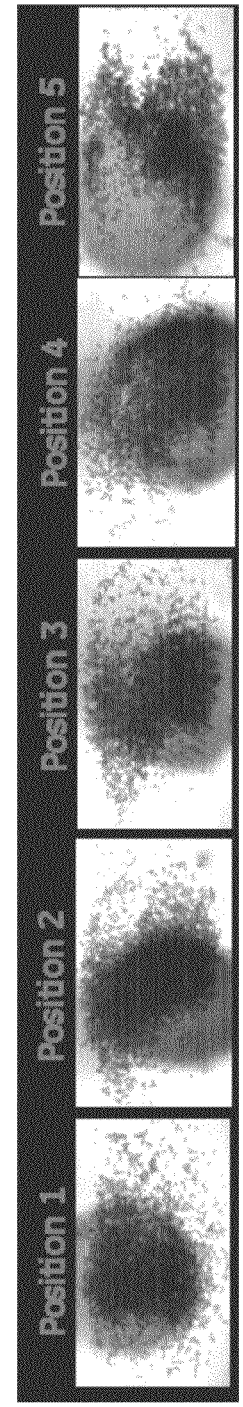
FIG. 11B is a series images of examples of bead distribution for the five micromagnets loaded for the same loading periods.

Each magnet may be used to capture one or a plurality of beads (e.g. 100's-1000's of functionalized beads). This subdivision of beads spreads the beads evenly across the channel and prevents clumping. As shown in FIG. 4, the magnet array is positioned across a network of microchannels. The biological targets that are subsequently loaded into the channels, after the beads are attached to the ends of the micromagnets (e.g. as shown in FIG. 1), depending on a given assay, have one or multiple opportunities to bind to the functionalized-beads as the targets flow across the beads. Once the target-containing sample flows across the magnetic bead array, each micromagnet can be individually released as shown in FIG. 2. Upon release, binding events from each micromagnet sub-assay can be assessed using downstream analytical components. FIGS. 11A and 11B illustrate how bead numbers can be controlled by adjusting the amount of time that beads are allowed to flow across each micromagnet. In the example shown in FIG. 11A, each magnet received the same loading time (15 minutes), and so the bead surface concentrations are substantially the same.

An embodiment of an array device of the invention is generally shown and referred to in FIGS. 1 and 2 as array 10. Array 10 comprises a plurality of micromagnets 12 seated in a fixture 16, and a primary magnet 14, wherein a portion of each micromagnet is in releasable operative association with a sample channel 18 and another portion of each micromagnet is in releasable operative association with the primary magnet. Array 10 further comprises a mask 16 that is variably interposed between one or more of the micromagnets and the primary magnet to prevent attraction between one or more of the micromagnets and the primary magnet, depending on the processing stage of an assay as it is run. The array may be integrated into a microfluidic device such as device 30 generally shown in FIG. 4.

Figure 3:
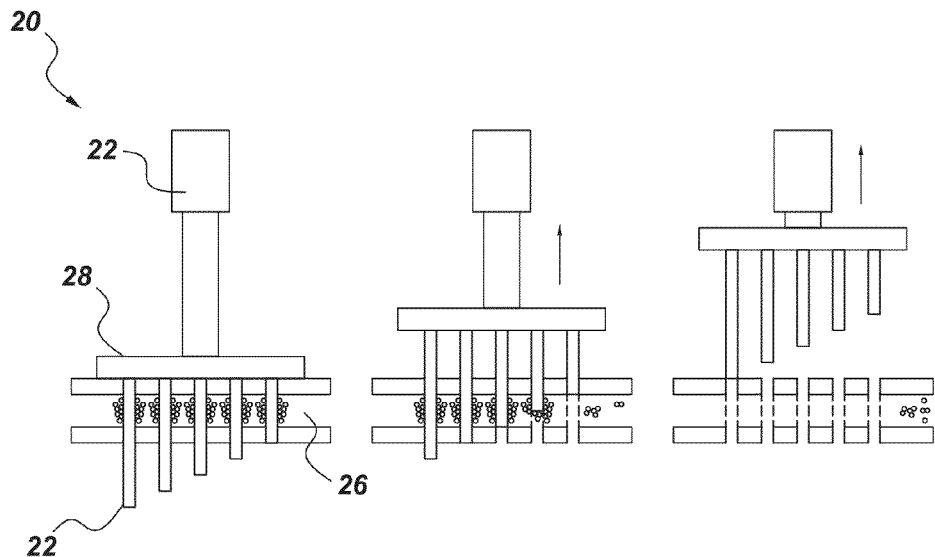
FIG. 3 is a top view drawing of a microfluidic device into which an embodiment of the array of the invention is integrated.

Another embodiment of an array device of the invention is generally shown and referred to in FIG. 3 as array 20. Array 20 comprises a linear actuator 22 to which a plurality of micromagnets 24 are operatively attached or permanently attached. The micromagnets 24 have different, stepped lengths as illustrated in FIG. 3, which shows the array device during a bead release operation. During a bead loading operation, actuator 22 moves towards flow channel 26, the distal end of the longest magnet is exposed to flow channel 26 first. Once the longest magnet is loaded with beads, actuator 22 is move further towards flow channel 26 so that the magnet having the next longest length is exposed to flow channel 26. These linear movements of actuator 26 are continued as needed to load beads onto the number of micromagnets needed for a given assay.

In the bead release operation illustrated in FIG. 3, the magnetic beads are attached to, and effectively trapped by, micromagnets 24 within microfluidic channel 26. The micromagnets extend through hollow cylinders 28 in channel 26. The operation, shown in FIG. 3 of this example, comprises a staged release of the beads from the micromagnets. The differing lengths of the micromagnets enable the beads to be variably release in stages as the linear actuator is moved away from channel 26, drawing the micromagnets from the channel. In a loading operation, the actuator and the micromagnets would be in opposite direction, towards the channel.

The micromagnets may be operatively attached, for example, if the distal portion 28 of the linear actuator is a magnetic seat, in which case the attraction between micromagnets 24 and the magnetic seat can be interrupted to release one or more of the micromagnets 24 from the magnetic seat. In the latter example, the lengths of the magnets could vary, as shown in FIG. 3, or they could be the same length. If the same length, movement of the magnets into or out from the channel may be initiated, for example, by engaging or disengaging each micromagnet from a magnetic seat fixed to the distal portion 28 of the actuator.

The size, shape, configuration and number of micromagnets may be varied depending on the application and size and shape of the microdevice. The device may also comprise one or more primary magnets and one or more masks of varying sizes and shapes, similarly depending on the application and size and shape of the microdevice.

Figure 5:
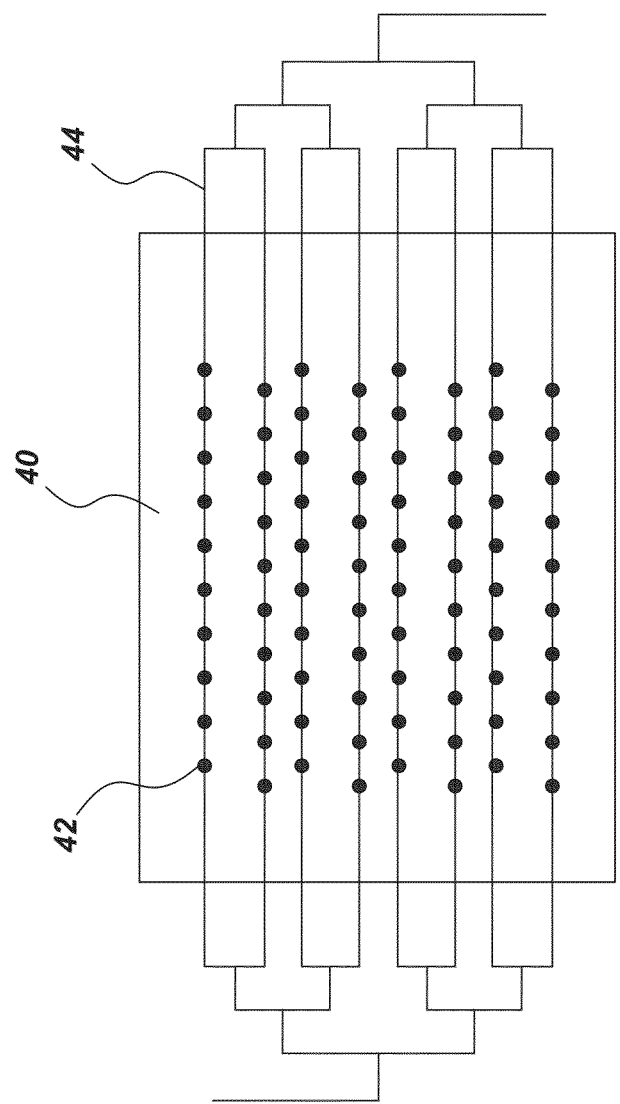
FIG. 5 is a schematic, top view, cross-sectional drawing of an embodiment of the magnet array of the invention interposed over a plurality of channels.

FIG. 4 is a schematic diagram of an embodiment of the magnetic array integrated into a microfluidic chip 30 that comprises two microfluidic modules, a sample preparation module 32 and a cytometer module 34. The sample preparation module 32 in this example comprises the magnetic array, also referred to as a trap port, and a fluidic manifold with five, 100 μL capacity reservoirs, each addressable by a valve. FIG. 5 is a schematic drawing of an embodiment of a micromagnetic array 40 comprising a plurality of micromagnets 42 is interposed over a plurality of fluidic channels 44.

Figure 8:
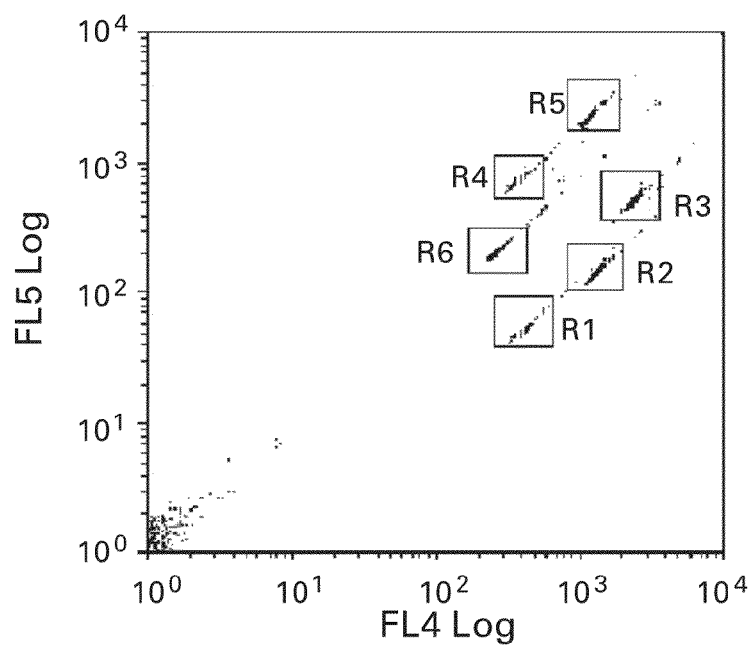
FIG. 8 is a plot of an example of bead classification in two emission channels (705 nm and 660 nm) for a set of magnetic, multiplexing beads
Figure 9:
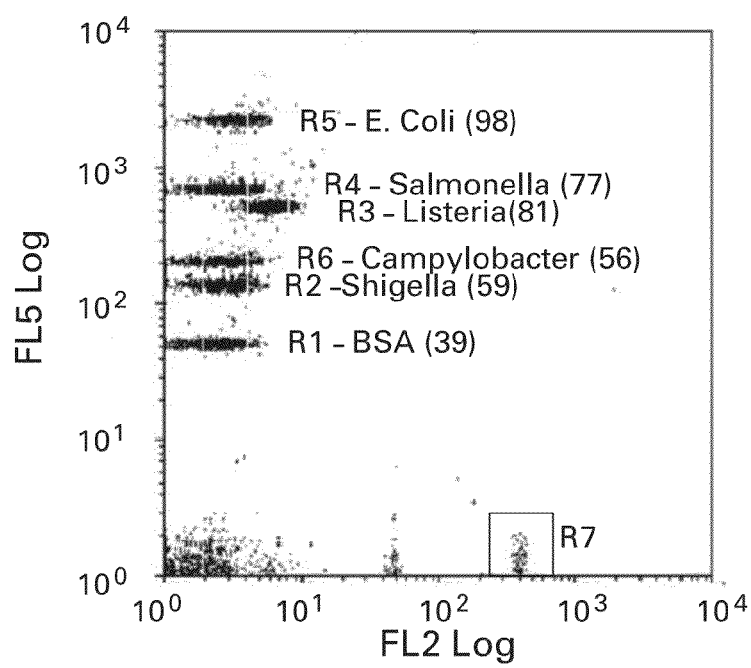
FIG. 9 is a plot of an example of control data from a target detecting channel (525 nm)
Figure 10:
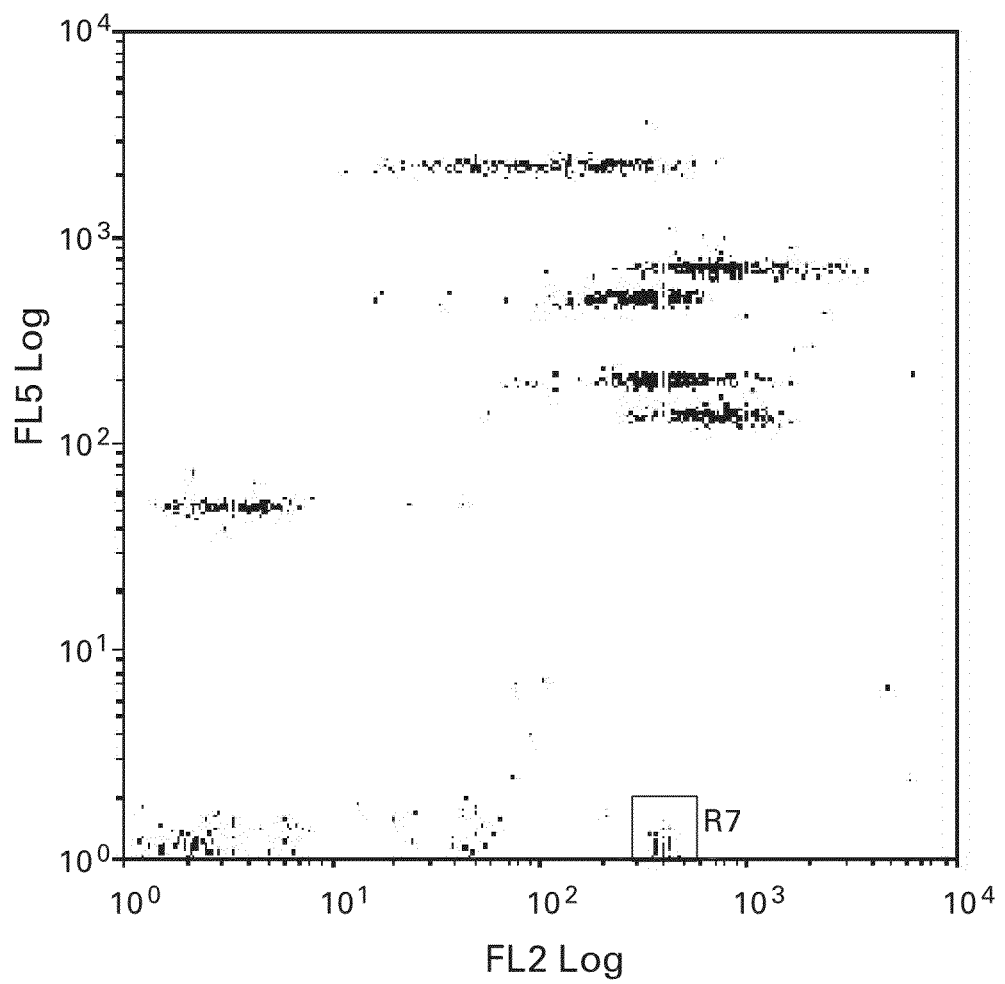
FIG. 10 is a plot of an example of bacteria detected from released beads after surface functionalization and bacteria capture.

The devices and methods of the invention may be integrated into a variety of microfluidic systems such as, but not limited to, microflow cytometry systems. For example, the devices and methods may be used in a cytometry system that carries out multiplexing processes such as the process for which the data shown in FIGS. 6-10 reflects. The data shown in FIGS. 8-10 reflects a five-plex bacteria detection process, which was carried out using an example of a device and method of the invention, and which achieved an automated sample-to-answer processing time of 30 minutes. The detection sensitivity and time period in which the processing takes place for a magnetic bead-based immunoassay run, as one example, is substantially similar to current manual assays.

In one example, the automated fluidic manipulations were performed using an elastomeric microvalve assembly, which was adapted from GE Healthcare's Biacore® System, to carry out the labeling and reaction steps for a sandwich-immunoassay. The fluidic driving and optical interrogation is performed within a compact instrumentation footprint, which offers substantial advantages over large and complex laboratory-based flow cytometers currently in use for medical diagnostics. The addressable micromagnet array in this embodiment uses active magnetic elements in the array to provide greater control during bead loading which results in an even distribution of beads throughout the fluidic channel. Moreover, active control of each magnet enables separate, group release of the 100's-1000's of beads trapped on each magnet, and direct injection into the downstream microflow cytometer. Efficiency is increased in part by spreading the surface reaction out across the entirety of a flow channel to enable batch-mode processing on each magnet. In the example reflected in FIGS. 8-10, the bacteria captured by these magnetic traps were released and analyzed in a flow cytometer. Each individual magnet was released separately, thus allowing a small subset of beads to pass through the cytometer after each release.

Figure 6:
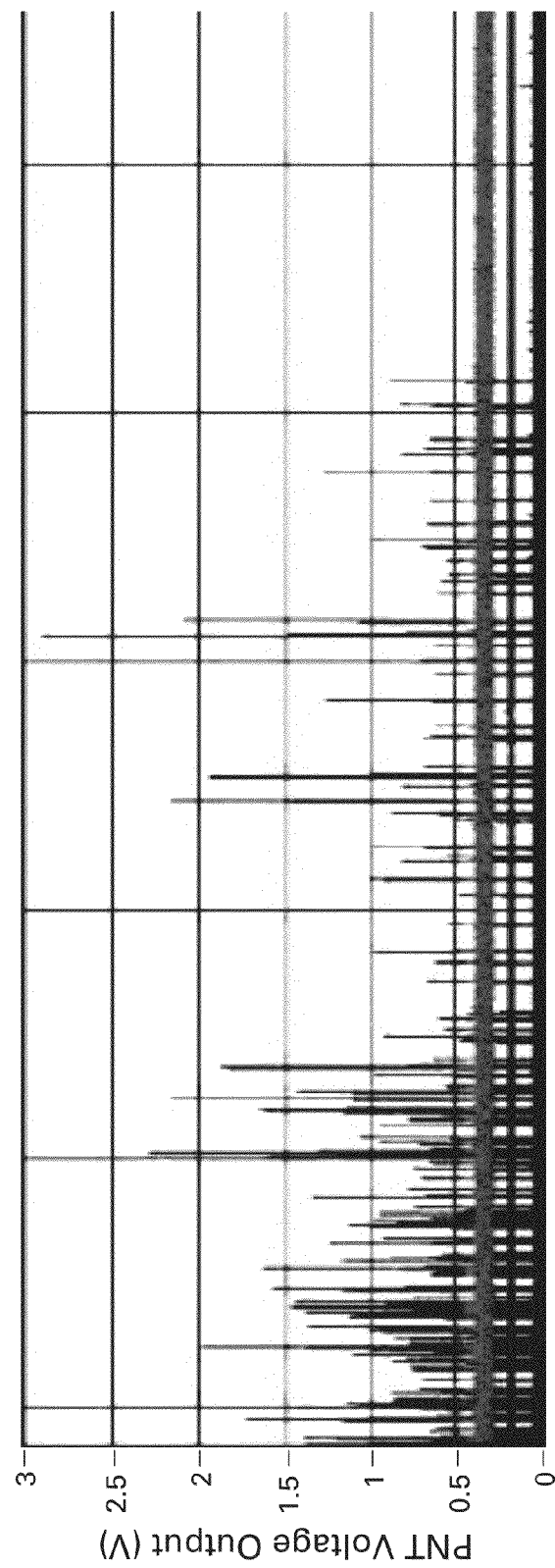
FIG. 6 is a graph of fluorescence data from magnet beads that have been released from a single magnetic trap.
Figure 7:
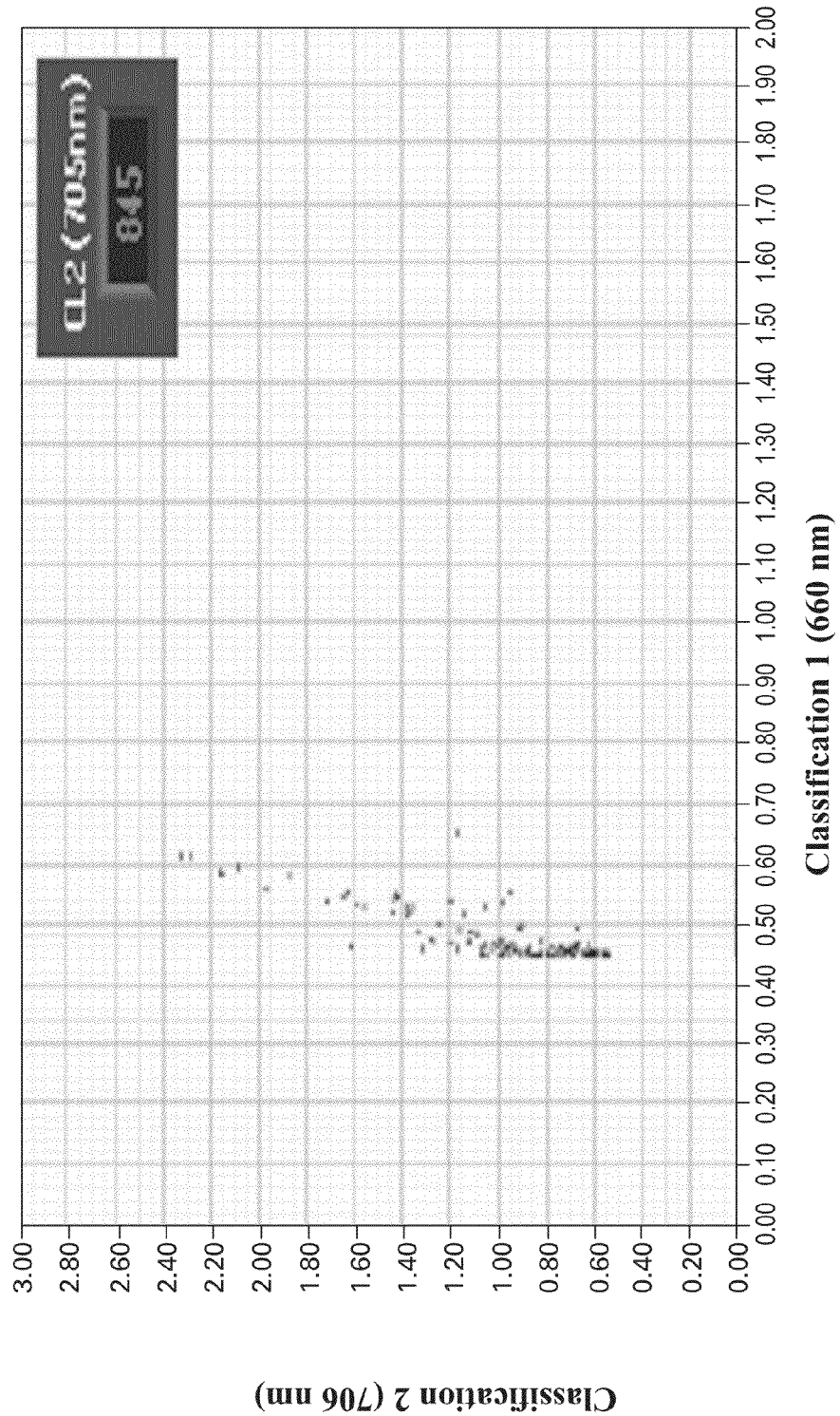
FIG. 7 is a plot of an example of a peak count for dual-labeled beads (705 and 660 nm emission), plus a peak count in the 705 channel.

FIG. 6 is a graph of the raw fluorescence signal from magnetic beads that have been released in discrete quantities from a single magnetic trap. Approximately 1000 beads are trapped on the magnet, which matches peak counts from downstream laser-induced fluorescence detection. The beads used in this example were dual-labeled (705 and 660 nm emission), and were functionalized with antibodies specific for certain bacteria which can be used to capture and detect the biological targets. FIG. 7 is the peak count plot for the dual-labeled beads, plus a peak count in the 705 nm channel.

The magnet devices shown in FIGS. 1-5 and the methods reflected by the data in FIGS. 6-11 are non-limiting examples. Other configurations and methods may be used to process magnetic beads in discrete batch-modes. Other non-limiting examples comprise a single magnetic capturing area that processes a small number of beads serially in smaller reaction volumes. A batch-mode system overcomes the challenges of smaller reaction volumes by forming the optimal ratio of magnetic beads to biological target in each sub-assay.

Figure 12:
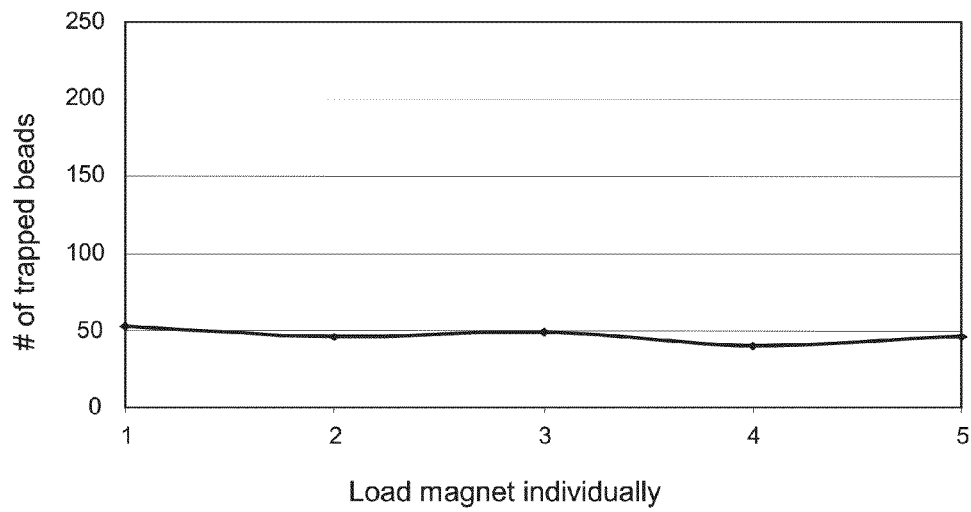
FIG. 12 is a graph showing an example of results when the micromagnets are loaded one at a time with a discrete number of beads
Figure 13:
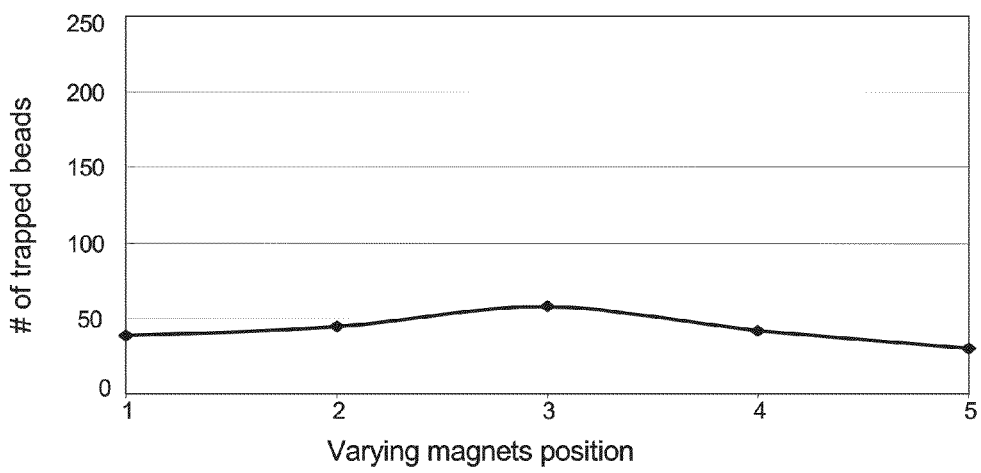
FIG. 13 is a graph showing an example of bead loading results when the distance between the magnets and the channel is varied.
Figure 14:
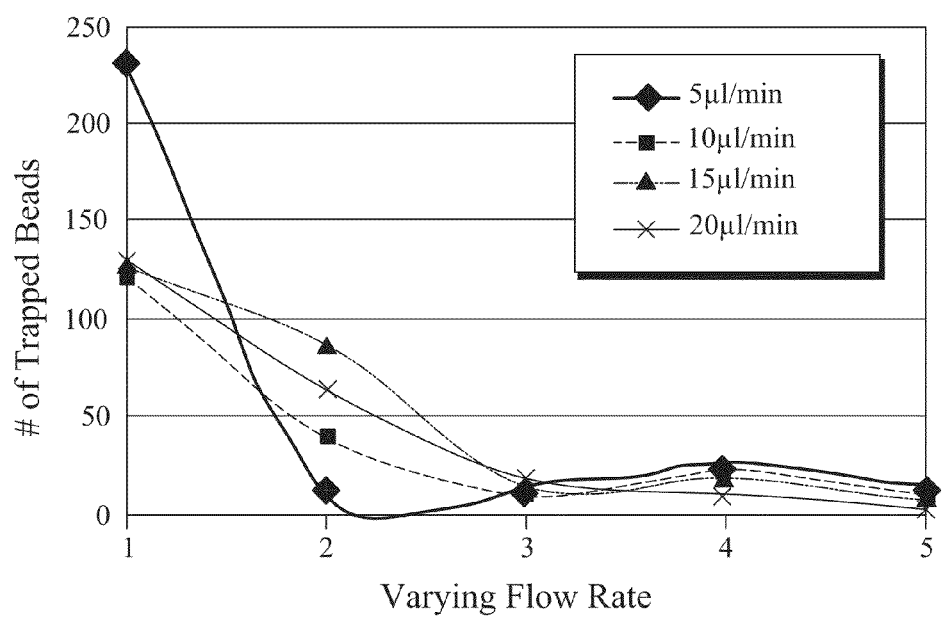
FIG. 14 is a graph showing an example of bead loading results when the flow rate of beads during a loading operation is varied.

The number of beads loaded on a given magnet may also be optimized by varying various loading parameters. For example, the micromagnets may be loaded one at a time, as shown in FIG. 12, depending on the requirements of a given assay, for example, when extremely precise batch processing is required. The micromagnets may also be loaded two or more at a time. The distance between the distal end of the micromagnets and the channel may be varied to adjust the bead loading parameters, as shown, for example, in FIG. 13. Increasing or decreasing the flow rate in the channel may also be used to adjust the number of beads that are loaded onto one or more of the micromagnets and to adjust or modified the binding rate of targets on the beads subsequent to loading the beads onto the magnets.

EXAMPLE

This example of the method uses the embodiment shown in schematic diagram in FIG. 4 comprising a magnetic array integrated into a microfluidic chip 30 that comprises the two microfluidic modules, sample prep module 32 and cytometer module 34. Sample preparation module 32 comprises a fluidic manifold with five, 100 μL capacity reservoirs, each addressable by a valve.

The active fluidic components used in this example were made using sterolithography. A fluidic control box was used, which, using both positive and negative pressure, was operated using four separate diaphragm pumps and an array of 16 solenoid valves for controlling the pneumatic valve lines. The sandwich-immunoassay was performed using a continuous flow by washing the pre-functionalized and trapped magnetic beads with each reagent. Carboxy-functionalized Luminex® microspheres (sets 56, 59, 77, 81, 98) were coupled to Goat-IgG, specific for *Shigella, Listeria, Salmonella, E. coli*, and *Campylobacter*. After the bacteria capture step, immunolabeling was completed by flowing biotinylated antibody and streptavidin-conjugated phycoerythrin through the device. Excitation light from diode lasers at 532 nm and 635 nm enabled both bead identification (emission: 705 nm and 660 nm) and quantification of bacteria (emission 565 nm). In separate runs, 200 or 500 μm magnets were housed in an array of cylindrical holes fabricated directly above the microfluidic channels (FIG. 5). A sliding mask interposed between the micromagnets and the primary magnet prevents the upper portion of the micromagnets from being attracted to the primary magnet located above or adjacent to the array of micromagnets. Each micromagnet was individually actuated to load and release the beads by moving the slide back and forth (depending on the stage of the operation) and close or open each respective pore in the micromagnet fixture to expose the upper portion of each micromagnet to the larger magnet. The micromagnets were reset by simply re-inserting the slide and breaking attraction to the larger magnet. Multiple runs were performed to determine the optimal conditions to load the array, and capture and release from individual micromagnets.

E. coli labeled within the sample preparation module resulted in a detection level of $6 \times 10^3$ CFU/mL (compare, for example, to $2 \times 10^3$ CFU/mL using manual processing). Unlike magnetic traps used for sample preparation in commercial cytometers, placement of the magnet directly upstream of the microflow cytometer resulted in high detection efficiencies of the trapped beads. The number of beads trapped and then counted, from each magnet position, was consistent for the various runs (689.33+/−80.21 for three separate runs). Unlike large-scale magnetic traps that are used for qualitative preconcentration of cells in cytometry applications, this level of sensitivity and consistency adequate for use in the quantitative detection of rare biological targets. The complete assay was performed in under 30 minutes, and was hands-free, in this example, except for the initial loading of the reservoir which otherwise can be readily automated using available reservoir loading systems. An alignment procedure may be performed at the on-set of the experiment by sending a small portion of the beads past the magnetic trap and into the cytometer portion of the device. Further processing was completed using the pressure source and valve control available in the fluidic control box. Speed of bead loading may be controlled, for example, based on the holding force of the magnetic trap. For example, bead loss may occur if flow rates exceed 5 uL/min during continuous flow processing.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A microfluidic device for batch processing magnetic bead assays comprising,
   one or more micromagnets seated in a fixture; and
   an actuator; wherein a first portion of each micromagnet is oriented towards a microfluidic sample channel, and a second portion of each micromagnet is releasably coupled to the actuator such that releasing the second portion from the actuator results in movement of the first portion of the micromagnet towards the microchannel.

2. The microfluidic device of claim 1, wherein the actuator comprises a primary magnet.

3. The microfluidic device of claim 2, further comprising a mask that is configured to be variably interposed between one or more of the micromagnets and the primary magnet to control a magnetic attraction between one or more of the micromagnets and the primary magnet.

4. The microfluidic device of claim 3, wherein the interposition of the mask is configured to be varied based at least in part on a processing stage of a microfluidic assay.

5. The microfluidic device of claim 3, comprising a plurality of masks.

6. The microfluidic device of claim 2, comprising a plurality of primary magnets.

7. The microfluidic device of claim 1, comprising a plurality of micromagnets.

8. The microfluidic device of claim 1, wherein the micromagnets are integrated into a microfluidic sample preparation module.

9. The microfluidic device of claim 8, wherein the microfluidic sample preparation module is integrated into a flow cytometry system.

10. The microfluidic device of claim 9, wherein the flow cytometry system is configured to detect functionalized magnetic beads.

11. The microfluidic device of claim 8, wherein the module is adapted to functionalize one or more magnetic beads.

12. The microfluidic device of claim 1, wherein the actuator is a linear actuator.

13. The microfluidic device of claim 12, wherein the linear actuator comprises a primary magnet to which the one or more of the micromagnets are releasably coupled.

14. The microfluidic device of claim 13, wherein one or more of the micromagnets are fixed to the primary magnet.

15. The microfluidic device of claim 13, further comprising a mask that is configured to be variably interposed between one or more of the micromagnets and the primary magnet to control a magnetic attraction between one or more of the micromagnets and the primary magnet.

16. A method for batch processing a microfluidic magnetic bead assay comprising,
   loading a plurality of magnetic microbeads into one or more microfluidic channels of a microfluidic device comprising a plurality of actuatable micromagnets; and
   initiating the microbeads to flow across one or more of the actuatable micromagnets in the loaded channel;
   capturing one or more of the microbeads on one or more of the micromagnets; and
   releasing the captured beads, from one or more of the micromagnets, into the channel via actuation of the actuatable micromagnets.

17. The method of claim 16, further comprising, initiating a flow of sample material into one or more of the channels and across one or more of the beads captured on the micromagnets, whereby at least a portion of the sample materials binds to one or more of the captured beads.

18. The method of claim 16, further comprising, interposing a mask between a primary magnet and one or more of the micromagnets, to control a magnetic attraction between one or more of the micromagnets and the primary magnet.

* * * * *